US008100865B2

(12) United States Patent
Spofforth (10) Patent No.: US 8,100,865 B2
(45) Date of Patent: Jan. 24, 2012

(54) HYPODERMIC SYRINGE WITH PASSIVE ASPIRATION FEATURE

(75) Inventor: Leonard Morris Spofforth, Wirral (GB)

(73) Assignee: Hambley Limited, Heswall, Wirral (GB)

( * ) Notice: Subject to any disclaimer, the term of this patent is extended or adjusted under 35 U.S.C. 154(b) by 192 days.

(21) Appl. No.: 10/311,505

(22) PCT Filed: Jun. 14, 2001

(86) PCT No.: PCT/GB01/02646
§ 371 (c)(1),
(2), (4) Date: Dec. 16, 2002

(87) PCT Pub. No.: WO01/95960
PCT Pub. Date: Dec. 20, 2001

(65) Prior Publication Data
US 2003/0187406 A1    Oct. 2, 2003

(30) Foreign Application Priority Data

Jun. 15, 2000 (GB) .................. 0014605.0
Jun. 16, 2000 (GB) .................. 0014712.4
Aug. 30, 2000 (GB) .................. 0020731.6
Dec. 6, 2000 (GB) .................. 0029715.0
Mar. 30, 2001 (GB) .................. 0108018.3

(51) Int. Cl.
*A61M 5/315* (2006.01)
(52) U.S. Cl. .................. 604/218; 604/229; 604/230
(58) Field of Classification Search .............. 604/82–92, 604/111, 181, 187, 189–201, 205, 218–222, 604/226–228, 232, 235–244, 310, 311, 229–230; 222/325–327, 386
See application file for complete search history.

(56) References Cited

U.S. PATENT DOCUMENTS

| | | | | |
|---|---|---|---|---|
| 2,526,365 A | * | 10/1950 | Jorgensen | 604/229 |
| 2,554,744 A | * | 5/1951 | Jorgensen | 604/229 |
| 3,045,674 A | * | 7/1962 | Goldberg | 604/228 |
| 3,224,445 A | * | 12/1965 | Melott | 604/228 |
| 3,295,525 A | * | 1/1967 | Evers Hans et al. | 604/415 |
| 3,340,872 A | * | 9/1967 | Cox | 604/229 |
| 3,583,399 A | * | 6/1971 | Ritsky | 604/232 |
| 3,618,603 A | | 11/1971 | Levenson | |
| 3,766,918 A | * | 10/1973 | Kessel | 604/125 |
| 3,890,956 A | * | 6/1975 | Moorehead | 600/578 |
| 3,910,273 A | * | 10/1975 | Arlers | 604/228 |
| 3,990,446 A | * | 11/1976 | Taylor | 604/210 |
| 4,084,588 A | * | 4/1978 | Koenig | 604/205 |
| 4,216,771 A | * | 8/1980 | Arlers et al. | 604/229 |

(Continued)

FOREIGN PATENT DOCUMENTS
FR    2764193    12/1998
(Continued)

*Primary Examiner* — Theodore Stigell
(74) *Attorney, Agent, or Firm* — Richard M. Goldberg (57) ABSTRACT

The invention comprises a disposable hypodermic syringe with means for passive aspiration. The syringe comprises a barrel (10) of clear synthetic plastics material and a plunger (12) comprising an elastic bung (28) slideable in the barrel (10). Pressure on the plunger elastically deforms the bung (28). If this pressure is released the bung (28) resiles to effect aspiration. This aspiration is passive, requiring no active withdrawal of the plunger by the user. After use the syringe may be disposed of as a whole, with no disassembly, using one hand only. The syringe may be made by adapting cartridges conventionally used for dental local anaesthetic.

24 Claims, 4 Drawing Sheets

U.S. PATENT DOCUMENTS

| | | | | |
|---|---|---|---|---|
| 4,221,218 A | * | 9/1980 | Pfleger | 604/218 |
| 4,270,536 A | * | 6/1981 | Lemelson | 604/110 |
| 4,333,456 A | * | 6/1982 | Webb | 604/121 |
| 4,333,457 A | * | 6/1982 | Margulies | 604/121 |
| 4,333,458 A | * | 6/1982 | Margulies et al. | 604/220 |
| 4,381,779 A | | 5/1983 | Margulies | |
| 4,500,310 A | * | 2/1985 | Christinger | 604/228 |
| 4,585,445 A | * | 4/1986 | Hadtke | 604/234 |
| 4,664,656 A | | 5/1987 | Taddei | |
| 5,139,490 A | * | 8/1992 | Vetter et al. | 604/201 |
| 5,195,985 A | * | 3/1993 | Hall | 604/195 |
| 5,314,416 A | * | 5/1994 | Lewis et al. | 604/219 |
| 5,350,367 A | * | 9/1994 | Stiehl et al. | 604/232 |
| RE34,845 E | * | 1/1995 | Vetter et al. | 604/243 |
| 5,411,488 A | * | 5/1995 | Pagay et al. | 604/218 |
| 5,411,489 A | * | 5/1995 | Pagay et al. | 604/218 |
| 5,413,563 A | * | 5/1995 | Basile et al. | 604/218 |
| 5,437,647 A | * | 8/1995 | Firth et al. | 604/110 |
| 5,688,252 A | * | 11/1997 | Matsuda et al. | 604/218 |
| 5,690,618 A | * | 11/1997 | Smith et al. | 604/232 |
| 5,693,027 A | | 12/1997 | Hansen et al. | |
| 5,716,339 A | * | 2/1998 | Tanaka et al. | 604/89 |
| 5,735,825 A | * | 4/1998 | Stevens et al. | 604/218 |
| 6,068,616 A | * | 5/2000 | Janus | 604/240 |
| 6,142,977 A | * | 11/2000 | Kolberg et al. | 604/218 |
| 6,227,371 B1 | * | 5/2001 | Song | 206/534 |
| 6,361,524 B1 | * | 3/2002 | Odell et al. | 604/187 |
| 6,416,323 B1 | * | 7/2002 | Grenfell et al. | 433/90 |

FOREIGN PATENT DOCUMENTS

WO    WO9530444    11/1995

* cited by examiner

HYPODERMIC SYRINGE WITH PASSIVE ASPIRATION FEATURE

BACKGROUND OF THE INVENTION

This invention concerns hypodermic syringes and particularly the safety thereof.

The safety of hypodermic syringes as addressed herein falls broadly into two categories, that is patient safety and practitioner safety, and these two matters will now be considered in turn.

When using a hypodermic syringe it is generally necessary for reasons of patient safety to check the position of the needle tip relative to blood vessels to ensure that potentially toxic material is not injected into the circulatory system. Intravascular injection gives rise to the risk of a toxic reaction, especially if administered quickly, when the injectant may travel around the body as a bolus to arrive at the brain in abnormally high concentration. This may happen with any injectant but is notably serious in the case of local anaesthesia, especially if the anaesthetic agent is combined with adrenaline, since adrenaline entering the circulation system may have fatal consequences. The danger is particularly severe in dental local anaesthesia because the injection site is so close to the patient's brain.

The standard method of checking the position of the needle tip relative to blood vessels is by a procedure known as aspiration. After the practitioner has inserted the needle, the plunger of the syringe is retracted by a small amount to obtain a sample of the surrounding body material. If the tip of the needle is in a blood vessel, a sample of blood will be drawn back into the syringe where it can be observed. Then, if blood is seen, the practitioner can begin again, altering the position of the needle. To allow for movement of the needle, aspiration may need to be repeated one or more times during the course of the injection.

There are two kinds of aspiration, active and passive. Active aspiration is a procedure in which the practitioner retracts the plunger manually. Active aspiration is somewhat awkward and may lead to movement of the needle, as well as of the plunger, making the aspiration uncertain. Passive aspiration (sometimes called "self-aspiration" which for the purposes of the present application is deemed to mean the same thing) is much safer. Passive aspiration is aspiration that takes place automatically when pressure on the plunger of the syringe is released, rather than the plunger having to be actively retracted. In other words, providing a syringe with means for passive aspiration means that the practitioner does not have to move the plunger manually to carry out the aspiration procedure. And this ensures that the injection site will be the same as the sampling site.

It is an object of the present invention to improve patient safety by providing a hypodermic syringe with passive aspiration.

The essential sharpness of hypodermic needles inevitably means that users occasionally injure themselves. Until comparatively recently, these so-called needlestick injuries were almost always no more than painful, and regarded as an occupational hazard by doctors, dentists and so forth. However perceptions have been changed by the spread of serious diseases such as auto-immune deficiency syndrome (AIDS) and hepatitis and the resurgence of tuberculosis in developed countries. Such diseases are readily transferred by needle and needlestick injuries are now perceived as potentially life-threatening. It will be understood that aspiration amplifies the threat by inducting a much greater amount of potentially infected material into the syringe.

The prevalence of needlestick injuries is indicated by a trade union estimate of twenty thousand such injuries a year in Scotland alone. The seriousness is reflected in data from UK occupational health departments showing eight hundred and thirteen reports of exposure to bloodborne viruses at work between July 1997 and June 2000. (And at least one practitioner caught HIV despite immediate prophylaxis). Official concern is marked by the Needlestick Safety and Prevention Act passed (unanimously) by the US Congress and signed into force in November 2000.

In dentistry it has been universal practice over many years to employ hypodermic syringes with needles that after use are resheathed, detached and placed in a container known as a sharps box for disposal. However the risk of a needlestick injury is present during the period between completing the injection and placing the needle in the sharps box. The risk is obviously greater if this period is extended—as when a practitioner puts a syringe aside after use (perhaps, understandably, to attend to the patient) instead of dealing with its disposal straight away. It is also, of course, not uncommon for a practitioner to compound the risk by passing the used syringe to a nurse or other assistant.

However the most acute, and avoidable, risk stems from post-injection disassembly, and in particular resheathing the needle. (Notably, regulations in USA prohibit resheathing of hypodermic needles but dentistry has a specific exemption). Disposability of the syringe as a whole will make it quick and easy for the practitioner to dispose of it immediately, and the needlestick risk will be substantially reduced. (The use of a disposable syringe in dentistry will also, of course, remove the need for the dental exemption).

It is therefore another object of the invention to improve practitioner safety by providing a hypodermic syringe which is disposable after use, that is as a wholes without the need to detach the needle or any other part.

At this point may be noted another aspect of patient safety which is particularly relevant to dental local anaesthesia. Dental surgeons invariably use a cartridge type of syringe which has a reusable actuating mechanism. A cartridge containing local anaesthetic agent—typically an amino-ester or an amino-amide mixed with a proportion of adrenaline—is loaded into a chamber of the actuating mechanism. The cartridge has a slideable bung arranged to be engaged by a plunger of the actuating mechanism when the cartridge is in the chamber. After the cartridge has been loaded into the chamber a needle is attached to its forward end, usually by means of a screw thread arrangement. Then the practitioner can depress the plunger to drive the bung into the cartridge and expel the contents thereof to make an injection in the usual way. After use, the cartridge and needle are disassembled and disposed of, and the actuating mechanism sterilised for reuse.

The problem in this, as will be appreciated by those knowledgeable in the science, is that certain disease vectors—such as the prion proteins associated with variant Creutzfeldt Jakob disease (VCJD)—can survive conventional sterilisation. It is therefore another object of the invention to provide a hypodermic syringe which does not require sterilisation after use.

A disposable syringe is the only effective safeguard against cross-contamination by way of the syringe, but the dental profession has not hitherto used disposable syringes for local anaesthesia. It will be appreciated, however, that a disposable syringe can go entirely into the sharps box waste container straight after use. And importantly, the dentist can do this using just the (one) hand holding the syringe, without exposing his/her other hand, any other part of his body or any ancillary (or even, as may be the case, another patient) to needlestick risk.

For the avoidance of doubt it should be observed that disposable syringes (which of course do not entail post-injection sterilisation) have been widely used over many years in medical and veterinary practice, but not in dentistry. By contrast, passive aspiration is well established in dentistry but not elsewhere. It is therefore a final object of the present invention to combine the benefits of disposability and passive aspiration to the advantage of all medical, dental and veterinary practice.

Certain previously known syringes will now be discussed.

In dental local anaesthesia the toxicity problem noted earlier has made pre-injection aspiration a standard recommendation—see, for instance, "Introduction to Dental Local Anaesthesia'" Mediglobe SA, 1990- and it was in this field that passive aspiration was first introduced, by Evers, more than thirty years ago. In U.S. Pat. No. 3,295,525 Evers et al disclose a hypodermic syringe of the cartridge type which is arranged to be automatically self-aspirating. The cartridge is provided with a bung having a bore extending through it to a resilient diaphragm at the head of the bung (that is, that part of the bung which engages the injectant in the cartridge). A specially designed nose on the end of the plunger in use extends through this bore to engage the diaphragm. When the plunger of the actuating mechanism is pressed the diaphragm is deflected inwardly and when the plunger is released the diaphragm automatically returns to its normal position, creating a pressure reduction within the cartridge to effect the desired aspiration. If aspiration is satisfactory the injection may proceed, the practitioner pressing the plunger further forward to cause a flange behind the nose to engage the bung and drive it into the cartridge and expel the injectant.

The Evers arrangement has a number of disadvantages. First, the requirement for a diaphragm complicates the manufacture of the bung. Second, the actuating mechanism has to be specially made or modified to provide the nose and the flange described above. Third, the special self-aspirating cartridge may only be used with this form of syringe. Fourth, the special syringe cannot be satisfactorily used with a standard cartridge because, without a bore in the bung, the extension may make the bung tip over and leak. And finally, the actuating mechanism is not disposable and, as noted earlier, its reuse requires sterilisation that is likely to be less than perfect.

In U.S. Pat. No. 4,216,771 Arlers et al disclose a hypodermic syringe with aspiration which is specifically stated to be a disposable article. However, this syringe does not provide passive aspiration. It has a plunger comprising circumferentially inner and outer parts connected together by a diaphragm at the head of the plunger. An aspiration rod is connected to the inner part and extends through a longitudinal channel in the plunger to an actuating member pivotally mounted at the outer end of the plunger. The practitioner effects aspiration by manually pivoting the actuating member to draw the inner part of the plunger backwards.

Aside from its complexity, with a number and variety of moving parts, the Arlers syringe offers active aspiration rather than passive aspiration. It therefore fails to secure the benefits of passive aspiration noted hereinbefore. In fact U.S. Pat. No. 4,216,771 points away from passive aspiration, criticising one previous arrangement (apparently the Evers syringe) as being difficult and awkward to use and another as being complicated and expensive. The present invention enables both these criticisms to be obviated.

An alternative to Evers's arrangement for passive aspiration, and more recent, is shown in U.S. Pat. No. 5,411,488 to Pagay et al. This discloses a syringe barrel pre-filled with injectant and closed by a slideable bung (or "plunger") of elastomeric material. The barrel has means at one end for attachment of a needle before making an injection. A plunger rod has a convex tip which fits into a blind bore in the bung and before use is connected thereto by a collar captive on the tip and formed with a screw thread for connection to the bung. The collar has limited sliding movement with respect to the plunger rod so that when the latter is depressed it first of all moves forward against the end of the blind bore to distort the head of the bung inwardly. If pressure on the plunger rod is then released the head of the bung returns to its normal shape, thereby effecting aspiration. Subject to satisfactory aspiration the plunger rod may then be depressed further, when a shoulder on the rod engages the collar screwed into the bung to drive the bung into the barrel and eject its contents.

Those skilled in the science will appreciate that Evers and Pagay provide aspiration in substantially the same way: in Pagay the convex tip of the plunger deforms the head of the bung just as in Evers the extended nose the plunger acts on the elastic diaphragm of the bung. It follows that Pagay's arrangement shares a number of the disadvantages noted above in relation to Evers. The provision of a screw thread in Pagay makes the bung even more complex. Similarly Pagay's plunger is complicated, and it requires the practitioner to connect it to the bung before an injection can be made. There is no mention of disposability in U.S. Pat. No. 5,411,488, but the very complexity of the plunger shown therein (and by inference its cost) suggests that practitioners would be encouraged to reuse it; and the persistence of certain disease vectors noted earlier makes this hazardous even with sterilisation. Significantly, thirty years elapsed between Evers and Pagay but there was no move towards combining disposability with passive aspiration in all that time, nor has there been in the years which have elapsed since Pagay.

SUMMARY OF THE INVENTION

According to the present invention there is provided a disposable hypodermic syringe including means for passive aspiration.

The term "disposable" is used herein to refer to a hypodermic syringe which is designed and made to be used once only and then disposed of as a whole, with no disassembly and no part retained. (A quasi-judicial definition of the term "disposable" may be derived from statutory regulations such as those of the European Union. For instance, the Medical Devices Directive, which is legally binding on all EU member states, requires that all medical devices be supplied with instructions as to their assembly, use and sterilisation or safe disposal, so that any medical device which is non-disposable must be accompanied by sterilisation instructions. It follows that a disposable hypodermic syringe is one that is classified as disposable under the Medical Devices Directive and supplied with disposability instructions.) Such disposability may be carried out by a practitioner using just one hand, with negligible risk of needlestick injury. The single use obviates sterilisation which is likely to be imperfect and may allow cross-contamination over a long time period. And passive aspiration is a safe and sure way of checking that the syringe is properly positioned in use. Thus the invention fulfils a long felt want in the practice of hypodermic injections by combining disposability with passive aspiration.

A disposable hypodermic syringe according to the invention preferably includes a barrel for injectant and a plunger depressible into the barrel to drive the injectant therefrom and is arranged so that depression of the plunger causes elastic deformation of part of the plunger within the barrel, whereby passive aspiration is provided.

The plunger may comprise a resilient bung in the barrel and a relatively rigid stem extending outwardly therefrom. The stem and the bung are preferably permanently connected together, and may be of unitary construction, possibly of similar elastomeric material (such as natural rubber or a synthetic plastics material) differentially treated to make the stem relatively rigid and the bung relatively elastic.

The bung may be formed with an elastically deformable diaphragm, to which the stem of the plunger may be attached. There may be a vent, possibly including a cavity, between the diaphragm and the interior of the syringe. Such a syringe may be arranged so that pressure on the plunger causes elastic deformation of the diaphragm towards the interior of the barrel and releasing said pressure allows the bung to resile and effect the required passive aspiration. The respective moduli of elasticity of the stem and the bung may be adapted to adjust the relative movement of the stem and the bung when the plunger is pressed.

Preferably the barrel of the syringe is transparent, and it may comprise a tube of clear synthetic plastics material. The barrel may contain a metered amount of injectant such as a local anaesthetic agent and be labeled to indicate the injectant and the amount.

A syringe according to the invention may comprise a seal closing the barrel, a hollow needle and connecting means such as a Luer lock or other screw thread for connecting the needle to the barrel in a first position, wherein the connecting means is adjustable to cause or permit the needle to move to a second position in which it pierces said seal. With this arrangement the needle may have a tip at one end for hypodermic intromission and a tail at the other for piercing said sea), and preferably the barrel, plunger, seal, needle and connecting means are after use disposable connected together.

A syringe according to the invention may alternatively have a needle permanently connected to its barrel.

A disposable hypodermic syringe according to the invention may be made by adapting a conventional cartridge for dental local anaesthetic, with only moderate modification of existing manufacturing plant, by securing to the forward end of said cartridge connection means for a hypodermic needle and securing to the rearward end of the cartridge an assembly comprising a slideable bung providing means for passive aspiration, a stem for sliding the bung and a cover providing a guideway for the stem. The connection means may be secured to the cartridge by a cap which also secures the conventional seal thereto.

The invention extends to apparatus for administering an injection, which apparatus comprises a sterile pack containing a hypodermic syringe according to the invention and prescribing information as to its use.

The invention also comprehends a method of guarding against cross-contamination in a hypodermic injection, which method comprises providing a hypodermic syringe with means for passive aspiration, using the means for passive aspiration to aspirate before performing the injection and disposing of the whole syringe immediately after performing the injection.

BRIEF DESCRIPTION OF THE DRAWINGS

Other features of the invention will be apparent from the following description, which is made by way of example only and with reference to the accompanying schematic drawings to an enlarged scale in which—

DETAILED DESCRIPTION

Figures 1, 2, 3:
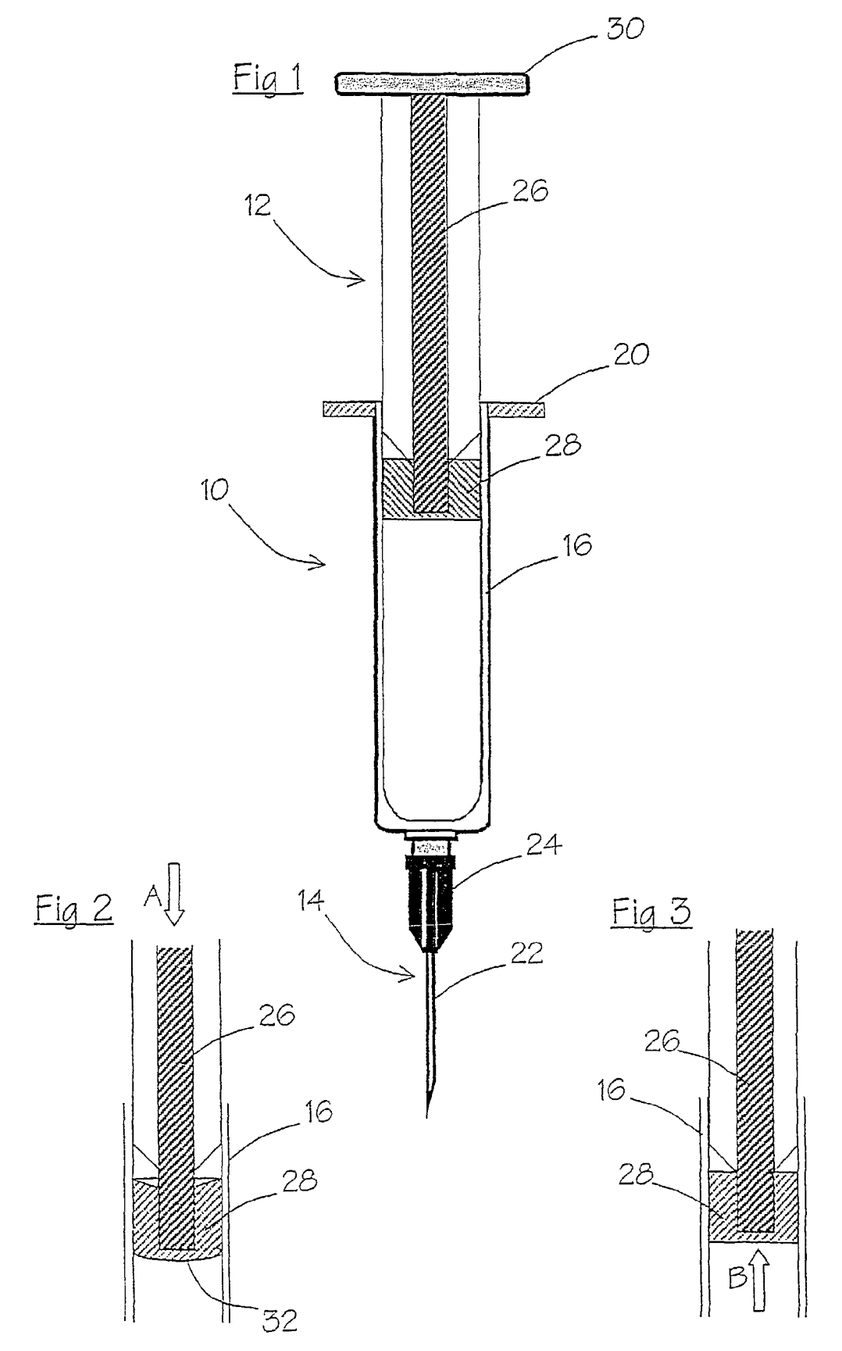
FIG. 1 is a cross section of a disposable hypodermic syringe including means for passive aspiration according to the invention.
FIG. 2 is a partial view showing the effect of applying pressure to the bung of the syringe shown in FIG. 1.
FIG. 3 is a partial view showing the effect of releasing pressure from the bung of the syringe shown in FIG. 1.

FIG. 1

Referring first to FIG. 1, a syringe comprises a barrel indicated at 10, a plunger indicated at 12 and a needle assembly indicated at 14.

The barrel 10 comprises a transparent tube 16 made of synthetics plastics material. The tube may contain a local anaesthetic agent or other medium to be injected, or it may alternatively be empty, eg to draw off a blood sample.

At one end the tube 16 is formed with a finger grip 20 extending laterally on both sides. The needle assembly 14 is at the other end of the barrel 10. It comprises a fine hollow needle 22 with its bore open to the interior of the barrel 10. The needle 22 is secured to the barrel in well-known fashion by a moulded collar 24.

The plunger 12 is of cruciform section with webs 25 extending radially outwards from a central stem 26 to provide a sliding fit for the plunger 12 within the bore of the tube 16. The stem 26 extends axially beyond the webs 25 and into a bung 28. The stem 26 is made of synthetic plastics material and is relatively rigid. The bung 28 is made of elastomeric material and is moulded on to the stem 26 to be permanently connected thereto. (The bung 28 may be fixed to the stem 26 by other means such as an adhesive; or it may be made of the same material as the stem and unitary therewith but differentially treated to alter its stiffness). The elasticity of the bung 28 allows the stem 26 slight axial movement relative to the bung 28 and against elastic deformation thereof. The bung 28 is a sliding fit within the tube 16 and its periphery sealingly engages the interior wall of the tube 16. (Although not shown, the bung 28 may be formed with peripheral rings or grooves to reduce sliding friction with the tube 16 whilst preserving the seal therewith). The plunger 12 includes an integrally moulded thumbpiece 30 at its outer end.

FIGS. 2 and 3

To use the syringe a practitioner holds it, using one hand only, with two fingers curled around the laterally extending finger grip 20 and the thumb of the same hand on the thumbpiece 30, and inserts the needle 22 into the target area. Referring now to FIG. 2, pressure on the thumbpiece 30 urges the stem 26 in the direction of arrow A. Before the bung 28 moves as a whole (that is, before thumb pressure overcomes the friction between the bung 28 and the tube 16) the relatively rigid stem 26 is displaced in a forward direction, distorting the bung 28 elastically. This creates a swelling 32 at the inner face of the bung 28. If the pressure on the thumbpiece 30 is now released, the bung 28 resiles elastically to its original shape, as shown in FIG. 3. The swelling at the inner face of the bung 28 subsides as indicated by arrow B. This creates a slight negative pressure within the tube 16, for aspiration.

It will now be understood that if the needle tip is in a blood vessel, this negative pressure will draw a sample of blood into the tube 16 where it can be seen by the practitioner. If it is intended that the needle tip be in a blood vessel the practitioner can continue; otherwise he can reposition the needle.

It will be noted that the elasticity of the bung 28 provides passive aspiration. In other words, by means of the invention aspiration takes place automatically when pressure on the thumbpiece 30 is released. There is no need to withdraw the plunger 12 manually.

After the injection is complete, the practitioner (still using just the one hand holding the syringe) can dispose of the whole syringe straight away by simply depositing it in a sharps box. There is no need for disassembly, and the procedure is so immediate that the practitioner will not be inclined to put the used syringe aside or pass it on to an assistant. Thus disposal is quick and easy and above all safe. And as no part of the syringe is retained for reuse there is no possibility of carry-over infection through inadequate sterilisation.

Figure 4:
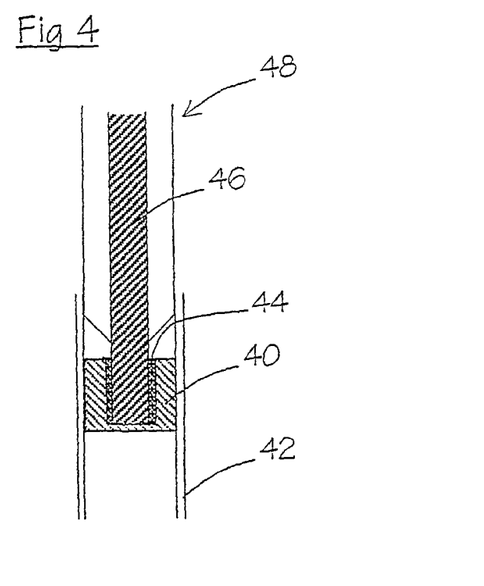
FIGS. 4 to 7 are partial views illustrating other means for passive aspiration in disposable syringes according to the invention.

FIG. 4

FIG. 4 shows another way of providing passive aspiration. An elastic bung 40 is slideable within a transparent tube 42 of synthetic plastics material. A sleeve 44 is interposed between the bung 40 and the stem 46 of a plunger 48. The sleeve 44 facilitates axial movement of the stem 46 relative to the bung 40, so that the stem 46 can be displaced with less pressure, and also strengthens the sealing engagement of the bung 40 with the tube 42. This means in turn that the friction between the bung 40 and the tube 42 can be reduced (eg by peripheral rings/grooves, the use of a softer elastomer and/or lubricant between the body and the tube), to make the injection movement easier and therefore smoother.

Figure 5:
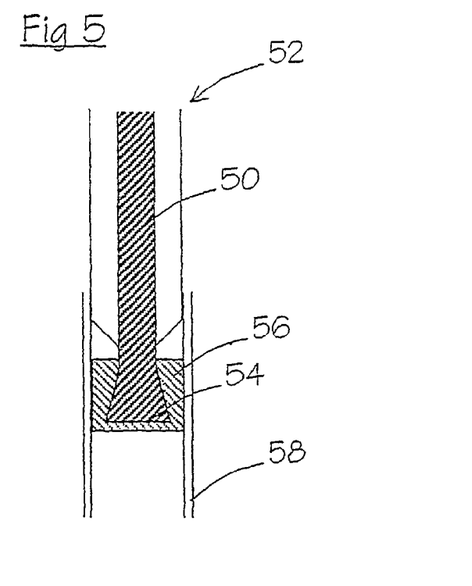

FIG. 5

FIG. 5 shows another way of making the injection movement easier. The stem 50 of a plunger 52 has a tapered enlargement 54 at its inner end that fits within a correspondingly shaped hole in an elastic bung 56. When the plunger 52 is urged into a transparent tube 58 by thumb pressure the interaction of the tapered enlargement 54 with the bung 56 it tends to contract the bung 56 so as to lessen its grip with the tube 58.

Figure 6:
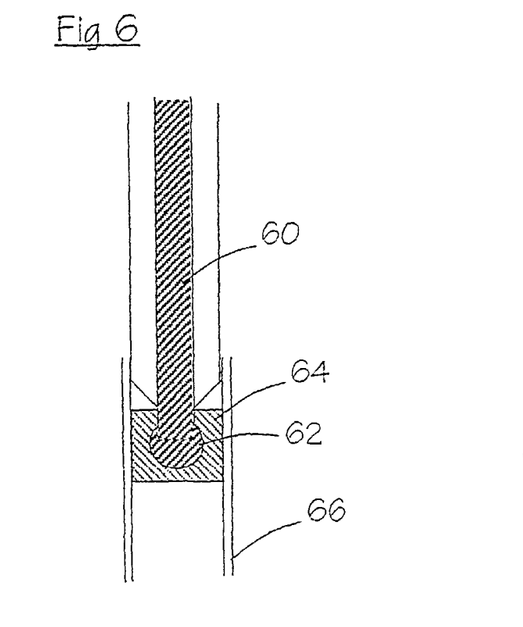

FIG. 6

FIG. 6 shows a modification of the design of FIG. 5. The syringe shown partially in FIG. 6 has a stem 60 with its inner end formed with a substantially spherical enlargement 62. The spherical enlargement fits within a correspondingly shaped hole in a bung 64 and the bung 64 is a sliding fit in a transparent tube 66.

As described with reference to FIGS. 1 to 6 the invention provides passive aspiration in a disposable hypodermic syringe through the elastic deformation and recoil of the head of the bung of the syringe (ie the face of the bung against the local anaesthetic agent within the syringe). This is not essential—indeed, the invention comprehends all kinds of passive aspiration in a disposable syringe—and another means of passive aspiration is shown in FIG. 7.

Figure 7:
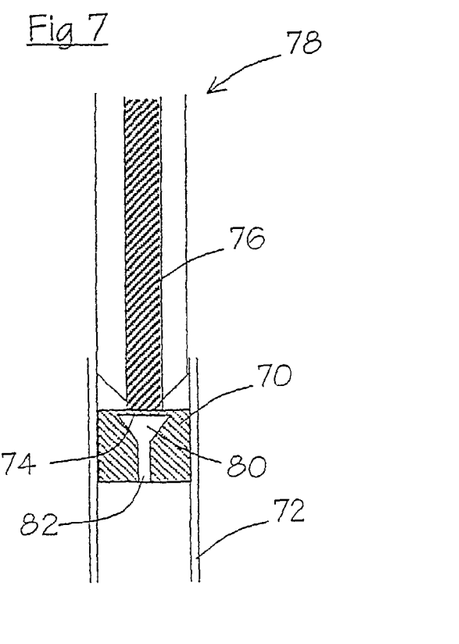

FIG. 7

Referring to FIG. 7, a bung 70 of natural rubber or other elastomeric material is slideable in a transparent tube 72 of synthetic plastics material. The bung 70 is formed on its outer side with a diaphragm 74 connected to the proximal end of the stem 76 of a plunger 78. (The stem 76 protrudes somewhat beyond the cruciform section of the plunger 78 to engage the diaphragm approximately centrally). On the inner side of the diaphragm 74 are a cavity 80 and a passage 82 extending to the inner face of the bung 70. Together the cavity 80 and passage 82 make up a vent between the diaphragm 74 and the interior of the tube 72, which contains an injectant not shown. When the plunger 78 is urged forward by thumb pressure the end of the stem 76 deforms the diaphragm 74 elastically inwards into the cavity 80 to reduce the volume thereof. It will be understood that the amount of flexing of the diaphragm 74 and thereby the change in volume of the cavity 80 depends upon the dimensions and the modulus of elasticity of the diaphragm 74. If pressure on the plunger 78 is now released, the diaphragm 74 recoils elastically to its original shape. Thus the cavity 80 opens up again and, by way of the passage 82, creates a slight negative pressure within the tube 72. This results in the aspiration required, which will be understood to be passive aspiration. Subject to satisfactory aspiration, the plunger 78 may now be depressed again to slide the bung 70 forwards along the tube 72 to inject the local anaesthetic agent. The diaphragm 74 is flexed again and remains flexed during the course of the injection, so aspiration may be repeated at any time by releasing the pressure on the plunger 78.

The arrangement shown in FIG. 7 may be modified to have a form of cavity different from that shown in FIG. 7. The cavity may for instance be substantially spherical. In the simplest form the cavity and passage may be merged so that the vent comprises a blind bore of substantially constant cross section extending from the diaphragm to the inside of the syringe.

Figure 8:
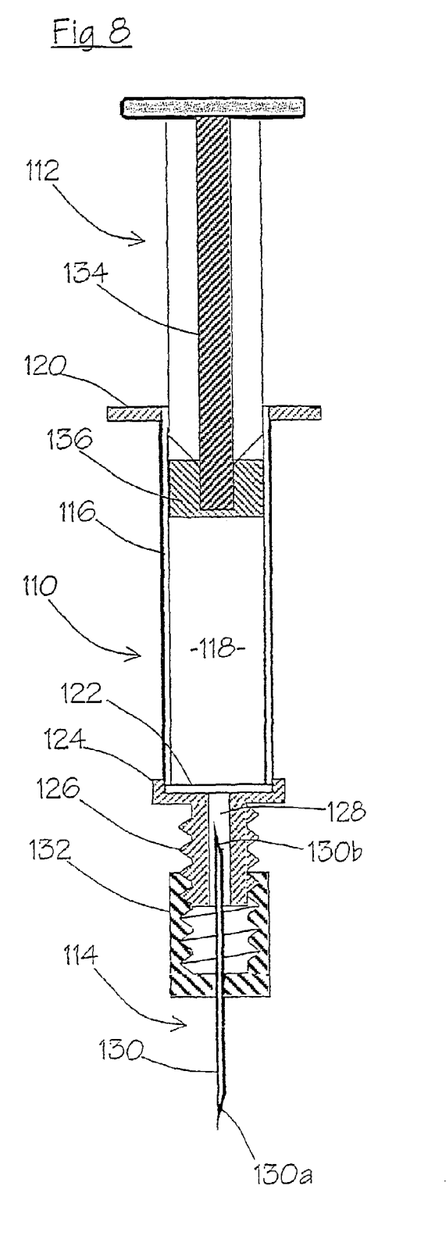
FIGS. 8 and 9 show in cross section means for attaching a needle of a disposable hypodermic syringe according to the invention.
Figure 9:
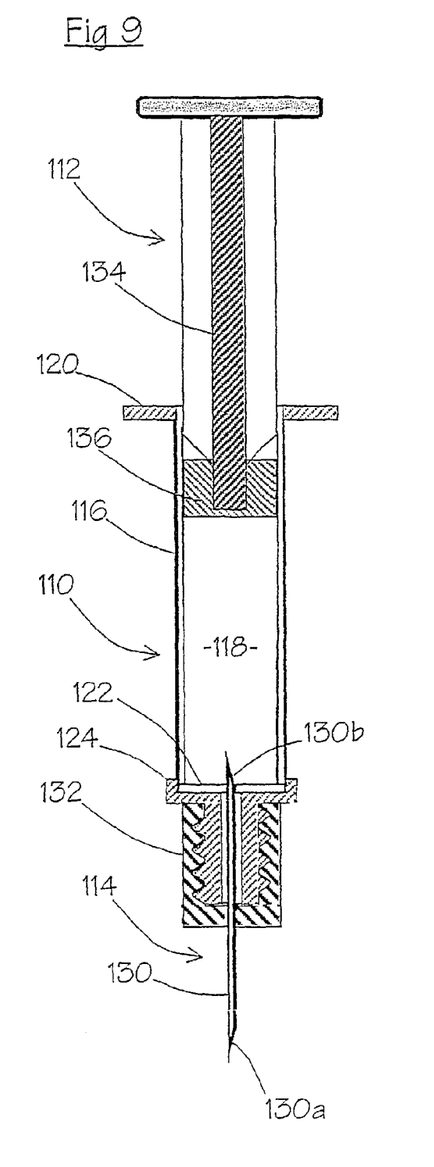

FIGS. 8 and 9

Referring now to FIGS. 8 and 9, these use the same reference numerals and are most conveniently considered together. The hypodermic syringe shown in the figures comprises a barrel indicated at 110, a plunger indicated at 112 and a needle assembly indicated at 114.

The barrel 110 comprises a transparent tube 116 made of synthetics plastics material. The tube 116 contains a measured amount of injectant 118 (such as, for instance, 1.8 ml of a local anaesthetic agent for use in dentistry). At one end the tube 116 is formed with a finger grip 120 extending laterally on both sides. At its other end the tube 116 is closed by a rubber seal (sometimes called a septum) 122 held in place by a cap 124 secured to the tube 116 in well known manner. The cap 124 is formed with a screw-threaded stud 126 having a central bore 128.

The needle assembly 114 comprises a fine hollow needle 130 secured in a collar 132. The needle 130 has a tip 130a and a tail 130b, both pointed. The collar 132 has an internal screw-thread matching that of the stud 126, whereby the needle assembly 114 is connected to the barrel 110.

As shown in FIG. 8, the collar 132 is partly screwed on to the stud 126. The needle 130 is then in a first position with its tail clear of the seal 122. It will be appreciated that the syringe may be transported as assembled in FIG. 8 because the seal 122 prevents leakage of the injectant 118 and/or prolonged contact with the needle 130 which may give rise to an adverse chemical reaction. Thus assembled a syringe may be supplied to a practitioner, in a sterile pack, prepared for use. Alternatively the syringe may be supplied separated from the needle assembly 114, which merely requires the practitioner to screw the collar 132 on to the stud 126. (Provided the components are supplied in a common sterile pack, the syringe qualifies for theatre use; and those skilled in the science will appreciate that it also avoids the risk of an inappropriate needle being fitted and an injection being administered to the wrong site with possibly catastrophic consequences).

To use the syringe, the practitioner screws the collar 132 home on the stud 126 so that, as shown in FIG. 9, the tail 130b of the needle 130 pierces the seal 122. In this second position of the needle 130, the plunger 112 may be pressed down to administer the injection 118 by way of the needle tip 130a.

It will be noted that the syringe shown in FIGS. 8 and 9 includes means for passive aspiration. The plunger 112 has a stem 134 extending into and secured to an elastic bung 136 slideable within the barrel 110. When the plunger 112 is pressed down, the stem 134 first of all slightly dilates the inner face of the bung 136. If the pressure is then released, this inner face resiles to effect aspiration. If the needle tip 130a is in a blood vessel, this negative pressure will draw blood into the tube 116 where it can be seen by the practitioner. If it is intended that the needle tip be in a blood vessel the practitioner can continue; otherwise he or she can reposition the needle.

When the procedure has been completed the whole syringe is disposed of, one-handed, simply by dropping it into an adjacent sharps box. Neither the practitioner nor any assistant is exposed to the potentially contaminated needle tip 130a. And sterilization-resistant vectors, as for VCJD, are overcome because the syringe is not used again.

Those skilled in the art will appreciate that the invention offers certain benefits additional to those hereinbefore described. For instance, having the stem 134 attached to the bung 136 means that if required the plunger 112 can be positively retracted, for instance to draw in solvent to mix with injection in powder form. Having the syringe pre-loaded with injectant allows the contents etc to be specified on the barrel 110, along with any warnings about use, which is much safer than marking merely the packaging, especially for dangerous drugs or injections requiring special precautions.

An important regulatory point may be noted here. Regulations generally require any drug to be supplied with prescribing information which must include information as to its disposal where appropriate. In effect, then, any syringe to be supplied pre-loaded with a drug must be disposable.

Various modifications to the syringe of FIGS. 8 and 9 may be made without departing from the essence of the invention. The tube 116 may be made of glass. The seal or septum 122 may be made of some material other than rubber. The cap 124 and the collar 132 may be made from light metal or synthetic plastics material and may be secured (respectively to the tube 116 and the needle 130) by bonding, crimping, heat-shrinking or otherwise. Further, the stud and collar shown in the drawing may be replaced by a friction fit connector, or by a Luer lock having a hollow collar and a rim fitting into an internal screw thread of a cap which has a tapered nose gripped by the hollow collar as it is screwed home.

As noted earlier herein, dental surgeons use a cartridge system for administering local anesthetics, and it follows that substantial manufacturing capacity is currently devoted to the production of cartridges. Whilst the present invention is among other things directed towards replacing the use of cartridges in dentistry by disposable syringes, it will be appreciated that it would not be sensible—either economically or logistically—to effect an instantaneous change. However it is possible for existing manufacturing plant to be progressively turned over to disposable syringes according to the invention, and this is illustrated in FIGS. 10 to 12.

Figures 10, 11, 12:
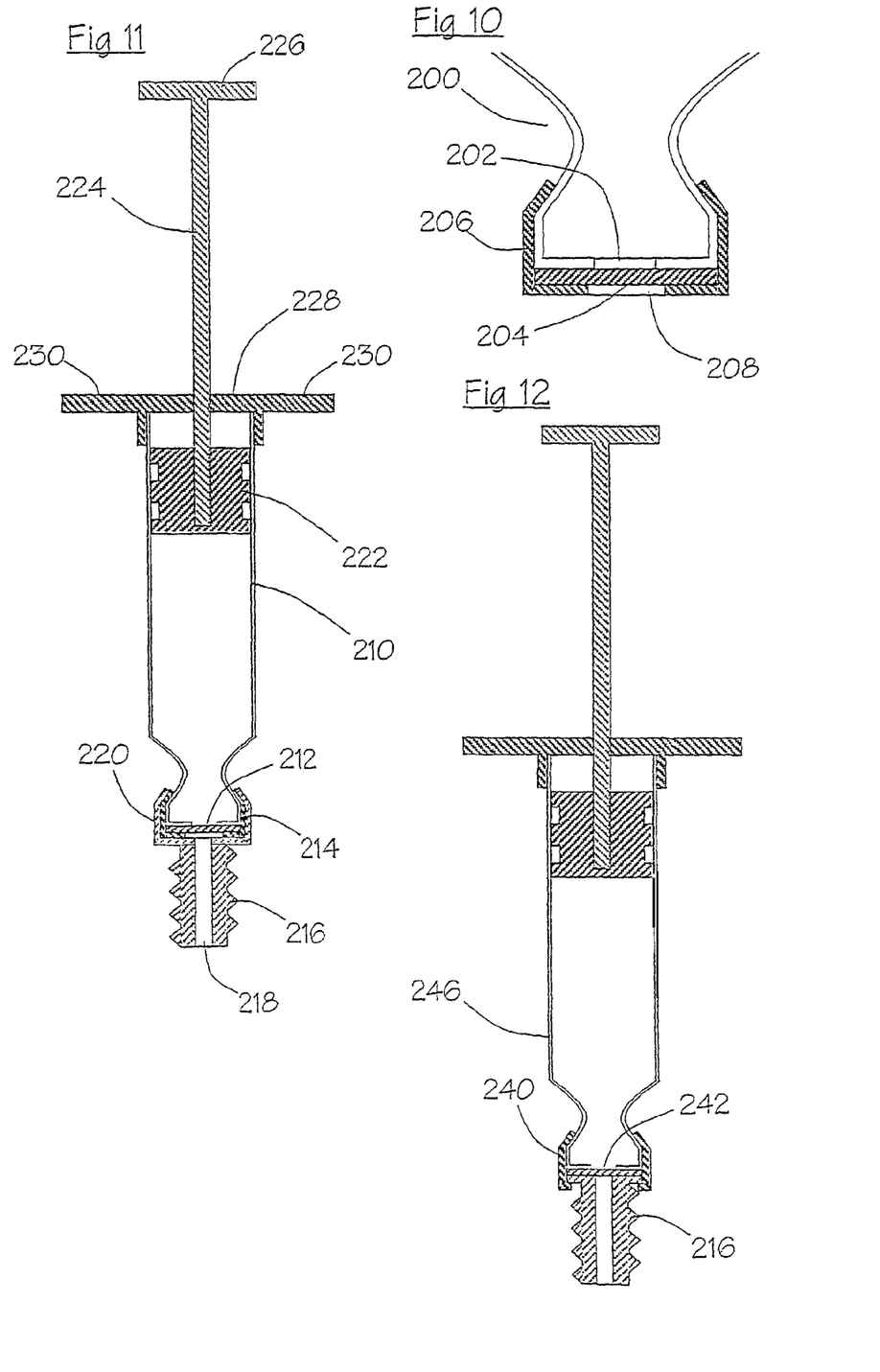
FIGS. 10 to 12 illustrate the adaptation of a conventional cartridge for dental anaesthetic to produce a disposable hypodermic syringe according to the invention.

FIG. 10

FIG. 10 shows, to a much enlarged scale, the forward part of a conventional cartridge for dental local anaesthetic. This cartridge is formed with a neck 200 (which is exaggerated in the drawing for the sake of clarity). The end of the cartridge is formed with a hole 202 covered by a seal or septum 204 keeping the anaesthetic secure and uncontaminated within the cartridge before use. (The other end of the cartridge is closed by a slideable bung, not shown). A metal cap 206 is swaged into the neck 200 or otherwise secured thereto to hold the seal 204 in place. The cap 206 is formed with a hole 208.

The use of cartridges is well known and does not require a detailed description here. Briefly, the cartridge is loaded into the chamber of an actuating mechanism (sometimes loosely called a syringe) having a plunger whereby the bung can be driven into the cartridge. A hypodermic needle is screwed on to the forward end of the actuating mechanism to pierce the seal 204 by way of the hole 208 in the cap 206, after which the system is ready for use. When the injection has been completed, the needle and the cartridge have to be detached and disposed of, and the actuating mechanism sterilised.

FIG. 11

FIG. 11 shows a first adaptation of a conventional cartridge to provide a disposable hypodermic syringe according to the invention. The cartridge 220 of FIG. 11 is of the form described above in relation to FIG. 10 and has at its forward end a seal 212 held in place by a metal cap 214. An externally threaded stud 216 formed with a through bore 218 is secured to the cartridge 210 by an integral skirt 220 swaged over the cap 214. The stud 216 is designed to receive a needle provided with an internally threaded collar, not shown, as hereinbefore described with reference to FIGS. 8 and 9, and it may conveniently be formed as a Luer lock.

At the other end of the cartridge 210 is mounted a plunger assembly comprising a slideable bung 222, a stem 224 extending therefrom to a thumbpiece 226 and a cover 228 formed with laterally extending finger grips 230. The cover 228 fits on to the rearward end of the cartridge 210 and is formed to provide a central guideway 232 for the stem 224. The bung 222, which is moulded on or otherwise secured to the stem 224, provides means for passive aspiration in the manner previously described herein.

The syringe of FIG. 11 can be made with little modification of existing plant for manufacturing the conventional cartridge. After the seal 212 and cap 214 have been applied to the cartridge 210 it is necessary only to attach the threaded stud 216 before filling the cartridge with a metered amount of local anaesthetic in the usual way and then add the assembly of bung 222, stem 224 and cover 228. (Two benefits of the cartridge system are that because the cartridge is preloaded in controlled conditions (a) there is no risk of cross-contamination from the filling procedure and (b) the contents are assured as to both quantity and quality, avoiding problems in this area when syringes supplied empty are filled locally by practitioners; and pre-loading syringes according to the present invention offers identical benefits).

FIG. 12

FIG. 12 shows a further adaptation of a conventional cartridge which is simpler but requires more modification of existing plant. In the arrangement of FIG. 12, a metal cap 240 is used to secure both the seal 242 and the threaded stud 216 to the cartridge 246. Compared with the arrangement of FIG. 11, this requires the stud 216 to be fitted one step earlier in the manufacturing process and the use of a cap 240 somewhat different and larger than the cap 214. In other respects the syringe of FIG. 12 is similar to that of FIG. 11.

The adaptation of a conventional cartridge may have a significant regulatory advantage. Where the cartridge is already approved for use, for instance under the CE system of the European Union, the additions described above in relation to FIGS. 11 and 12 need not be submitted to prolonged and expensive approvals procedures because these additions are non-invasive and therefore subject to self-certification by the supplier.

Those knowledgeable in the practice of injections will appreciate that the invention offers a simple and inexpensive hypodermic syringe with the benefits of disposability and passive aspiration. A syringe according to the invention is safe to use because, broadly speaking, disposability protects the practitioner and passive aspiration protects the patient—and this combination of features satisfies regulators and insurers. Further, syringes according to the invention can readily be made by adaptation of conventional cartridges, with commercial and regulatory benefits.

What is claimed is:

1. A hypodermic syringe comprising:
an axially extending barrel filled with injectant, which injectant is sealedly contained in the barrel between a fixed seal closing a forward end of the barrel and a slidable bung closing a rearward end of the barrel,
a connecting arrangement mounted on and extending forwardly from the forward end of the barrel for locking a hypodermic needle thereto so that the needle pierces said seal,
a plunger stem extending rearwardly from the bung to be manually pressed to slide the bung axially into the barrel to displace injectant therefrom by way of the needle piercing the same, wherein
the bung has a periphery in sealing engagement with the barrel and an inner face comprising a resiliently deformable portion which is elastically deformed axially forwardly when the plunger stem is manually pressed and which resiles axially rearwardly if the manual pressure is removed thereby to effect passive aspiration in use,
the bung includes an arrangement within said periphery that applies radial pressure on said periphery to strengthen the sealing engagement thereof with the barrel, and
the needle is locked to the barrel, the bung is retained in the barrel and the plunger stem is formed as a single unitary structure with the bung such that the plunger stem is unreleasably secured to the bung so that the assembly thereof cannot be dismantled and is thereby disposable as a whole after use.

2. A hypodermic syringe as claimed in claim 1, wherein said portion of the bung comprises an elastically deformable diaphragm.

3. A hypodermic syringe as claimed in claim 2, wherein the bung is formed with a vent between the diaphragm and an interior of the syringe.

4. A hypodermic syringe as claimed in claim 3, wherein the vent includes a cavity adjacent the diaphragm.

5. A hypodermic syringe as claimed in claim 4, wherein the stem is attached to the diaphragm.

6. A hypodermic syringe as claimed in claim 2, wherein pressure on the plunger stem causes elastic deformation of the diaphragm towards an interior of the barrel and releasing said pressure allows the bung to resile and effect the aspiration.

7. A hypodermic syringe as claimed in claim 6, wherein respective moduli of elasticity of the stem and the bung are adapted to adjust relative movement of the stem and the bung when the plunger stem is pressed.

8. A hypodermic syringe as claimed in claim 1, further comprising a sleeve between the stem and the bung.

9. A hypodermic syringe as claimed in claim 1, wherein the barrel is transparent.

10. A hypodermic syringe as claimed in claim 9, wherein the barrel comprises a tube of clear synthetic plastics material.

11. A hypodermic syringe as claimed in claim 1, wherein the barrel contains a metered amount of injectant.

12. A hypodermic syringe as claimed in claim 11, wherein the injectant includes a local anaesthetic agent.

13. A hypodermic syringe as claimed in claim 1, wherein the barrel is labeled to indicate the injectant and the amount of injectant.

14. A hypodermic syringe as claimed in claim 1, wherein the connecting arrangement connects the needle to the barrel in a first position, and the needle is adjustable thereon to move to a second position in which it pierces said seal.

15. A hypodermic syringe as claimed in claim 1, wherein the needle has a tip at a forward end thereof for hypodermic intromission and a tail at a rearward end thereof for piercing said seal.

16. A hypodermic syringe as claimed in claim 1, wherein the barrel, the connecting arrangement, the bung, the stem, the seal and the needle are after use disposable connected together.

17. A hypodermic syringe as claimed in claim 1, wherein the needle is permanently connected to the barrel.

18. A hypodermic syringe as claimed in claim 1, wherein the plunger stem is formed as a monolithic, single piece, unitary structure with the bung.

19. A hypodermic syringe as claimed in claim 1, wherein the arrangement in the bung includes a sleeve interposed between the bung and stem and which facilitates axial movement of the stem relative to the bung, while also providing radial pressure that strengthens sealing engagement of the bung with the barrel.

20. A hypodermic syringe as claimed in claim 1, wherein the arrangement in the bung facilitates axial movement of the stem relative to the bung so that the stem can be displaced with reduced pressure.

21. A hypodermic syringe comprising:
a barrel including injectant,
a connecting arrangement fixed to a forward end of the barrel for connecting a hypodermic needle thereto,
a bung closing a rearward end of the barrel and slidable into the barrel in use to displace injectant therefrom by way of the needle,
a plunger stem permanently connected to the bung and extending rearwardly therefrom to be manually pressed to slide the bung into the barrel, the stem and the bung being of unitary construction, and the stem and the bung being made of similar elastomeric material differentially treated to make the stem relatively rigid and the bung relatively elastic,
the bung having a resiliently deformable portion which is elastically deformed forwardly when the plunger stem is manually pressed and which resiles rearwardly if the manual pressure is removed thereby to effect passive aspiration in use, and
said hypodermic syringe being disposable as a whole after use.

22. A hypodermic syringe as claimed in claim 21, wherein the stem and the bung are made of synthetic plastics material.

23. A hypodermic syringe comprising:
an axially extending barrel filled with injectant, which injectant is sealedly contained in the barrel between a fixed seal closing a forward end of the barrel and a slidable bung closing a rearward end of the barrel,
a connecting arrangement mounted on and extending forwardly from the forward end of the barrel for locking a hypodermic needle thereto so that the needle pierces said seal, a plunger stem extending rearwardly from the bung to be manually pressed to slide the bung axially into the barrel to displace injectant therefrom by way of the needle piercing the same, wherein the bung has a periphery in sealing engagement with the barrel and an inner face comprising a resiliently deformable portion which is elastically deformed axially forwardly when the plunger stem is manually pressed and which resiles axially rearwardly if the manual pressure is removed thereby to effect passive aspiration in use, the bung includes an arrangement within said periphery that applies radial pressure on said periphery to strengthen the sealing engagement thereof with the barrel, and the needle is locked to the barrel, the bung is retained in the barrel and the plunger stem is unreleasably secured to the bung so as to be inseparable therefrom without breakage, so that the assembly thereof cannot be dismantled and is thereby disposable as a whole after use and such that if the structure of the plunger stem and the bung is broken apart, the syringe is unusable.

24. A method of administering a subcutaneous injection by means of a hypodermic syringe comprising an axially extending barrel filled with injectant, which injectant is sealedly contained in the barrel between a fixed seal closing a forward end of the barrel and a slidable bung closing a rearward end of the barrel, a connecting arrangement mounted on and extending forwardly from the forward end of the barrel for locking a hypodermic needle thereto so that the needle pierces said seal, a plunger stem extending rearwardly from the bung to be manually pressed to slide the bung axially into the barrel to displace injectant therefrom by way of the needle piercing the same, wherein the bung has a periphery in sealing engagement with the barrel and an inner face comprising a resiliently deformable portion which is elastically deformed axially forwardly when the plunger stem is manually pressed and which resiles axially rearwardly if the manual pressure is removed thereby to effect passive aspiration in use, the bung includes an arrangement within said periphery that applies radial pressure on said periphery to strengthen the sealing engagement thereof with the barrel, and the needle is locked to the barrel, the bung is retained in the barrel and the plunger stem is unreleasably secured to the bung so as to be inseparable therefrom without breakage, so that the assembly thereof cannot be dismantled and is thereby disposable as a whole after use and such that if the structure of the plunger stem and the bung is broken apart, the syringe is unusable, said method comprising the steps of:
  a) subcutaneously introducing the needle into a patient's body at an intended site,
  b) manually pressing and releasing the plunger stem to effect passive aspiration at said site,
  c) adjusting the position of the needle according to the results of the aspiration,
  d) in the adjusted position, manually pressing the plunger stem to slide the bung into the barrel and thereby deliver the injection,
  e) withdrawing the syringe to remove the needle from the patient, and
  f) disposing of the syringe as a whole without being able to release the plunger stem from the bung without breakage.

* * * * *